(12) United States Patent
Dykes et al.

(10) Patent No.: US 8,158,062 B2
(45) Date of Patent: Apr. 17, 2012

(54) DISPOSABLE FLUID SAMPLE COLLECTION DEVICE

(76) Inventors: Chris Dykes, Columbia, MD (US); Ben Lane, Phoenix, MD (US); Mike Abbott, Christiansburg, VA (US); Brian Murphy, Baltimore, MD (US); Eva Dixon, Columbia, MD (US); Brian Bean, Baltimore, MD (US); Brian Lipford, Belair, MD (US); Samuel Reed, North Garden, VA (US)

( * ) Notice: Subject to any disclaimer, the term of this patent is extended or adjusted under 35 U.S.C. 154(b) by 997 days.

(21) Appl. No.: 10/578,453

(22) PCT Filed: Nov. 5, 2004

(86) PCT No.: PCT/US2004/036909
§ 371 (c)(1),
(2), (4) Date: Apr. 12, 2007

(87) PCT Pub. No.: WO2005/046437
PCT Pub. Date: May 26, 2005

(65) Prior Publication Data
US 2008/0025872 A1 Jan. 31, 2008

Related U.S. Application Data

(60) Provisional application No. 60/517,573, filed on Nov. 5, 2003.

(51) Int. Cl.
*B01J 19/00* (2006.01)
(52) U.S. Cl. ......... 422/68.1; 422/50; 422/400; 422/401; 422/62; 422/502; 204/409; 324/438; 324/439
(58) Field of Classification Search .................. 422/50, 422/400, 401, 402, 403, 412, 60, 61, 62, 422/63, 64, 65, 66, 67, 502, 55, 4, 430, 68.1; 204/403, 409; 324/438, 439
See application file for complete search history.

(56) References Cited

U.S. PATENT DOCUMENTS

| 5,096,669 | A * | 3/1992 | Lauks et al. | 204/403.02 |
| 5,257,984 | A * | 11/1993 | Kelley | 422/918 |
| 6,379,929 | B1 * | 4/2002 | Burns et al. | 435/91.2 |
| 6,759,007 | B1 * | 7/2004 | Westberg et al. | 422/44 |

* cited by examiner

*Primary Examiner* — In Suk Bullock
*Assistant Examiner* — Sharon Pregler
(74) *Attorney, Agent, or Firm* — Ober, Kaler, Grimes & Shriver; Royal W. Craig

(57) ABSTRACT

A fluid sampling device (100) that operates by a combination of capillary action to collect a small fluid sample, and by pressure differential when inserted into an analyzer (200) to expose the fluid sample for testing by the analyzer (200). The device is especially suited for use as a disposable blood sampling unit designed to interface with a blood analyzer, albeit the concept of the invention may be employed for sampling and testing virtually any fluids.

13 Claims, 10 Drawing Sheets

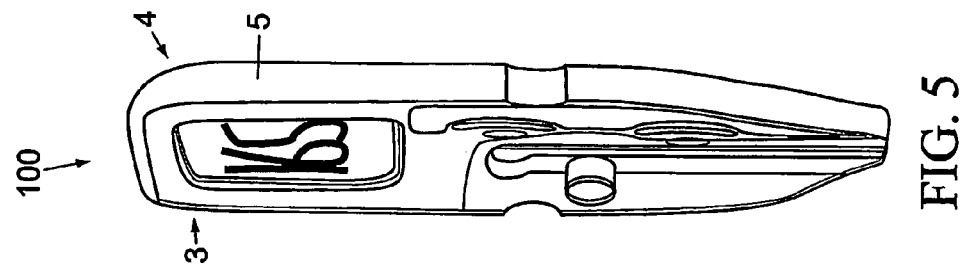
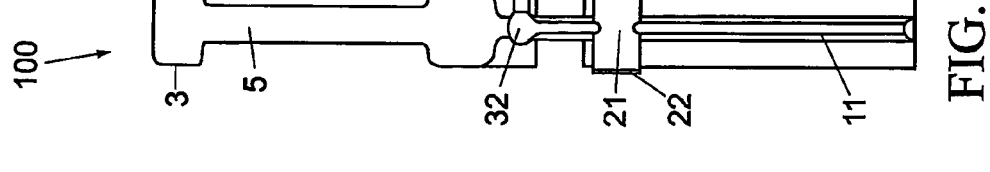
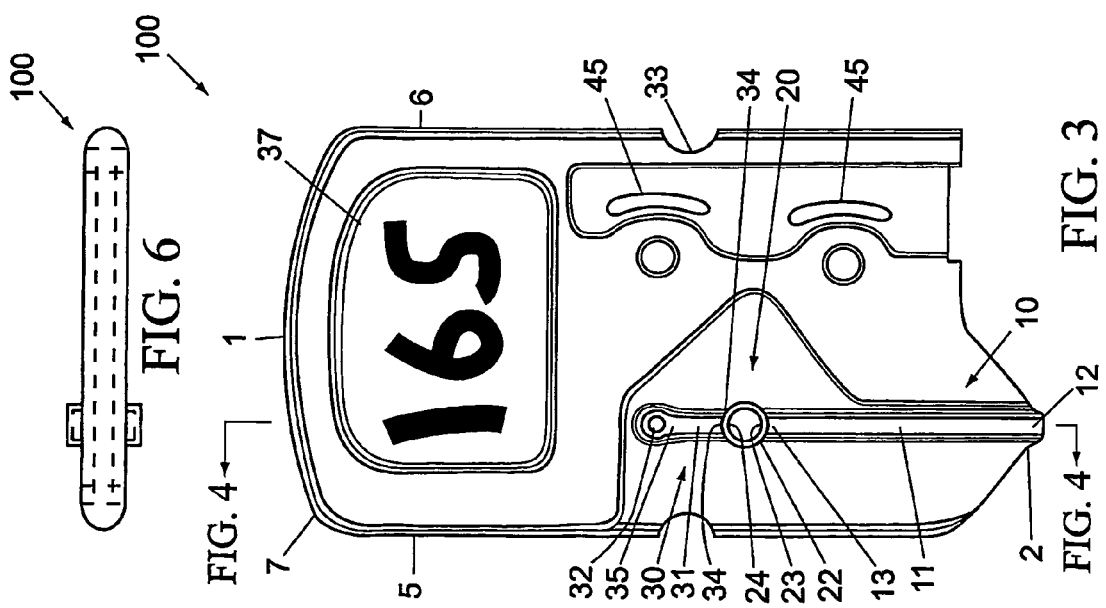

DISPOSABLE FLUID SAMPLE COLLECTION DEVICE

CROSS-REFERENCE TO RELATED APPLICATIONS

The present application derives priority from U.S. provisional application Ser. No. 60/517,573, filed Nov. 5, 2003.

BACKGROUND OF THE INVENTION

1. Field of the Invention

The invention relates to a method and apparatus for on-the-spot sampling of small amounts of fluid for analysis. More particularly, it relates to a disposable device that operates by a combination of capillary action to collect a small fluid sample (such as blood), and by pressure differential when inserted into an analyzer to move the fluid into and out of a test chamber, exposing the fluid sample for testing by an analyzer.

2. Discussion of the Background

Physicians routinely test blood parameters as part of the diagnostic process. The complete blood count (CBC) is the most common of these tests. Physicians use the results to assess the quantity and the condition of the blood's cellular components. Three of the elements of the complete blood count are used to describe the size and number of red blood cells in the sample: the hematocrit (HCT), the mean corpuscular volume (MCV), and the red blood cell count (RBC). Four more blood properties describe the oxygen-carrying capacity of the red blood cells: the hemoglobin concentration (HGB), total protein concentration (TPC), the mean cellular hemoglobin (MCH), and the mean cellular hemoglobin concentration (MCHC).

These blood properties, in particular HCT or HGB, can be used to diagnose anemia, acute blood loss, dehydration, and scores of other conditions. HCT or HGB can also be used to assess the oxygen carrying capability of the blood.

In the hospital environment, medical personnel typically collect blood samples and then transfer the sample to a central blood lab for analysis. Two well-known methods of collecting blood samples include: (1) collecting the sample into a capillary tube following a finger, heel, or earlobe stick, and (2) collecting the blood sample into a vial using a syringe. Capillary tubes are made of glass or hydrophilic plastic open at both ends. One end of the tube is placed against the site of a small incision on the finger, heel, or ear lobe, and blood flows into the tube from the incision by capillary action. In either case the capillary tube or vial containing the blood sample is delivered to the lab where an automated system performs the testing.

Recently, research and development in the area blood collection and testing has been conducted in light of: (1) the risks associated with transfer of blood between containers including contamination of the blood sample and the increased risk to medical or laboratory personnel of exposure to blood-borne communicable diseases, such as hepatitis B, hepatitis C, and HIV; and, (2) the need and desire for accurate on-the-spot analysis of blood samples in emergency situations, blood banks, or in office or home environments. As a result, a variety of portable blood analyzers have been developed which are capable of taking optical, electrical conductivity or ultrasonic readings of a blood sample in order to measure blood components and characteristics such as hematocrit, hemoglobin, mean corpuscular volume, red blood cell count, mean cellular hemoglobin, mean cellular hemoglobin concentration, and total protein concentration. These portable blood analyzers have in turn engendered a need for a single-use disposable device that serves as a collection receptacle, temporary storage container, and testing chamber for blood samples to be used in conjunction therewith.

The general concept of a disposable blood sample collector, which uses capillary action to draw blood from the site of a finger stick or the like, and then transfers the blood to another container or chamber within the same device for centrifuging, is known. The following prior art references illustrate this concept. U.S. Pat. No. 4,314,570 to Sarstedt discloses a disposable blood sample collector and storage receptacle having a short capillary tube communicating with a somewhat larger chamber. The chamber is filled, the capillary tube is disconnected, and the chamber containing the blood sample is placed in a centrifuge or tested directly. U.S. Pat. No. 5,472,671 to Nilsson et al. discloses a two cavity blood sample collection device. A blood sample is collected into the first cavity by capillary action and may be mixed with a reagent. The blood sample is then transferred by centrifugal force through a channel into a second cavity. Different reactions/analyses can be carried out in the different cavities. U.S. Pat. No. 5,916,814 to Kenney discloses a pre-sealed integral hematocrit test assembly. The assembly essentially comprises a holder for holding together both a blood sample tube and hematocrit test tube during centrifugation, whereby the blood from the sample tube is funneled into the test tube and separated into columns.

Additional devices, which are designed for both collection and testing (other than centrifuging) of blood, are also known. For example, typical home-use blood glucose monitors involve the user inserting a test strip into a monitor, lancing their finger, squeezing out a drop of blood, aiming the drop of blood so that it lands on the small test surface of the test strip. U.S. Patent Application 2003/0007893 of Purcell discloses a testing device for on-the-spot blood glucose monitoring (i.e. by photometric, colorimetric or electrochemical analyzers) that attempts to ensure that the user collects the necessary volume of blood with minimal air bubbles. Purcell developed an elongated test sensor insertable into a monitor. The sensor has a higher volume pick-up area at one end and a lower volume read area at the other. The read area end is inserted into the monitor. A blood sample from a finger stick is dripped onto and collected in the pick-up area of the test sensor. If the pick-up area volume is filled, an amount of blood required for testing will necessarily flow by capillary action through a transfer area and into a read area containing a reagent, where the monitoring unit reads the results. A cover over the transfer and read areas protects the monitoring unit.

Lastly, the concept of transferring a fluid sample from a collection area to a testing area within a device using a pressure differential is known. U.S. Patent Application 2003/0118479 of Quirk et al. discloses a device that is attached and sealed to a removable test strip (coated with a reagent) forming a testing chamber into which a collected blood sample can be directed towards or away from by inducing a pressure differential on the sample.

None of the above devices provide an all-in-one disposable device that collects and temporarily safely stores a blood sample for analysis, and which is insertable into the testing region of a portable analyzer to thereby seal the testing surfaces, forming a sealed testing chamber, and which incorporates or interfaces with an actuator which initiates a pressure differential to move the blood sample into and out of the testing chamber. The unique structure of this device used in conjunction with an analyzer provides a quick, clean and safe way of collecting and testing a predefined amount of blood (or other fluid), especially in emergency or non-laboratory settings.

SUMMARY OF THE INVENTION

Accordingly, one object of the present invention is to provide methods and devices for collecting a fluid sample of a predetermined amount for analysis.

It is another object of the present invention to provide methods and devices for temporarily storing the collected fluid sample.

It is another object of the present invention to provide methods and devices specifically adapted for collecting and storing blood samples and for analyzing the samples therein safely and efficiently.

It is another object of the present invention to provide a disposable blood sampling device that automatically collects a blood sample in a collecting region, and which automatically shifts the blood sample to a testing region.

It is another object of the present invention to collect a blood sample in a collecting region made of hydrophilic plastic tubing which inducts the blood by capillary action.

It is another object of the present invention that the capillary tube is of a predetermined length and diameter to ensure that slightly more than the necessary amount of blood is collected.

It is another object of the present invention that the capillary tube is clear or translucent and is visibly marked with lines to indicate to the user that the necessary amount of blood has been collected.

It is another object of the present invention to provide methods and devices suitable for a blood draw of less than 1 ml, and preferably using a drop of capillary blood as opposed to venous blood.

It is another object of the present invention to provide a disposable blood sampling device suitable for interfacing with a battery-operated, portable, hand-held blood analyzer.

It is another object of the present invention to provide a disposable blood sampling device that is insertable into a portable blood analyzer such that the testing region of the blood sampling device seals with testing surfaces of the blood analyzer to form a hermetically-sealed testing chamber.

It is a further object of the present invention that the testing chamber be in the shape of a cylinder with a square horizontal cross-section to minimize bubble formation.

It is another object of the present invention to provide a disposable blood sampling device with an integral pressure-differential actuator that is activated once the device is inserted into analyzer to cause blood to flow between the capillary collection tube and the testing chamber.

It is another object of the present invention to provide a disposable blood-sampling device that is activated once the device is inserted into analyzer by a pressure differential created by the analyzer, which causes blood to flow between the capillary collection tube and the testing chamber.

It is another object of the present invention to provide a disposable blood sampling device adapted for insertion into an analyzer to measure blood components and characteristics such as hematocrit (HCT), hemoglobin concentrations (HGB), mean corpuscular volume (MCV), red blood cell count (RBC), mean cellular hemoglobin (MCH), mean cellular hemoglobin concentration (MCHC), or total protein concentration (TPC).

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIGS. 3-6 illustrate a front view, section view, front-side perspective, and end view, respectively, of the disposable sampling device 100 of FIGS. 1-2.

DESCRIPTION OF THE PREFERRED EMBODIMENTS

Figure 1:
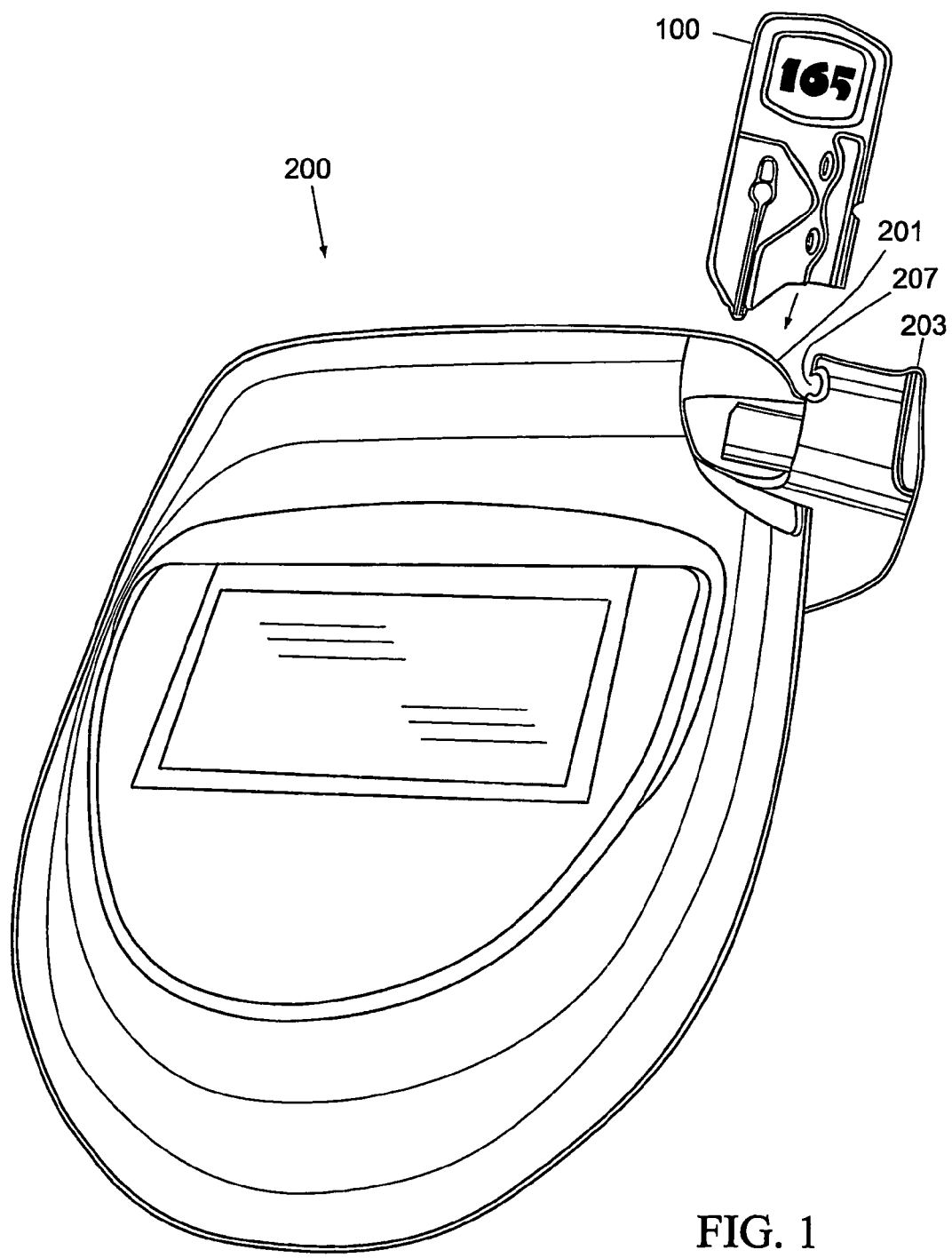
FIG. 1 is a perspective illustration of a preferred embodiment of the disposable device 100 next to an exemplary portable blood analyzer 200.

The present invention is a fluid sampling device that operates by a combination of capillary action whereby it collects a small fluid sample, and by pressure differential when inserted into an analyzer to transport the fluid sample to a testing region, where the fluid sample is exposed for testing by the analyzer. The device is herein described in the context of a disposable sampling device 100 for blood sampling that is designed to interface with a blood analyzer 200 as shown in FIG. 1. One skilled in the art will understand that the concept of the invention may be employed for sampling and testing virtually any fluid. The sampling device 100 is suitable for collecting 0.05 mL or less (1 drop) of blood, and is adapted for insertion into the analyzer 200 for testing by optical measurement, electrical conductivity measurement, ultrasonic testing, or any other established means. The preferred embodiment of the present invention 100 (as shown in FIG. 1) is shown with the ULTRACRIT™ ultrasonic high accuracy blood analyzer 200 designed by Key Technologies, Inc. and manufactured by Separation Technology, Inc., which is described in published PCT Application PCT/US2003/026889. This analyzer 200 includes an insertion bay 201 with pivoting and latching closure 203 for seating and sealing of the sampling device 100.

The sampling device 100 is first used to collect a drop of blood by capillary action, and is then inserted into the analyzer 200 for testing. The closure 203 is hinged to the main body of the analyzer unit 200 and after being opened, closes against a spring bias and latching shut to capture and seat the sampling device 100 inside bay 201. The closure 203 is formed with a track (not shown) which aligns with the sampling device track for catching and centering the sampling device 100.

Figure 2:
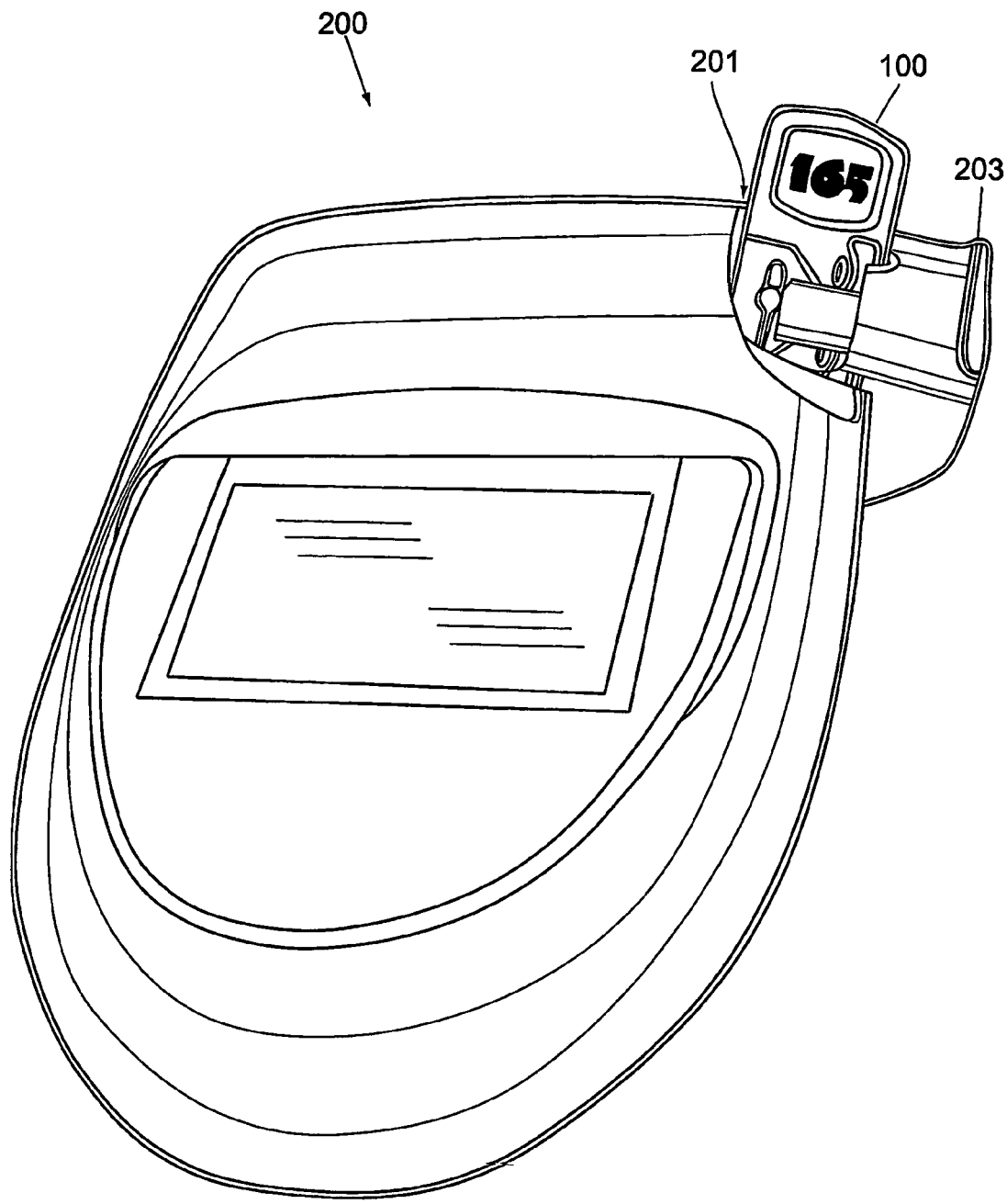
FIG. 2 is a perspective illustration of the disposable device 100 inserted into the portable blood analyzer 200 as in FIG. 1.

FIG. 2 illustrates the closing of closure 203 against the main body of the unit 200 against a spring bias. When fully closed, the closure 203 will latch shut to lock the sampling device 100 in place, squeezed tightly between two walls of the sampling chamber inside the analyzer 100. The latching of the closure 203 in turn activates a microswitch (not shown) that begins the actual testing procedure. It is extremely important for present purposes that the sampling device 100 be perfectly aligned and securely seated inside bay 201. The structure of the disposable sampling device 100 works synergistically with the latching action of the closure 203 to facilitate this, as described in more detail below.

FIGS. 3-6 illustrate a front view, section view, front-side perspective, and end view, respectively, of the disposable sampling device 100 of FIGS. 1-2. The sampling device 100 generally comprises an elongate and relatively thin rubber supporting frame 7 including a top end 1 and bottom end 2, front 3 and back 4, opposing sides 5 and 6, and formed with various functional features discussed below. The functional features of the sampling device 100 are sectioned into three primary regions, a collecting region 10, a testing region 20, and an actuator region 30. The entirety of sampling device 100 may be molded of Pebax™ rubber by Atofina Co., or any other flexible elastomer.

The collecting region 10 comprises an entrance aperture 12 defining the entrance to the capillary tube 11 that, in the preferred embodiment, is a hollow hydrophilic cylindrical tube with a volume of approximately 50 micro-liters (this is suited for collecting approximately 1-2 drops of blood). However, depending on the particular analyzer for which the device is designed, the volume of the capillary tube 11 may vary from between 0.01-1 ml. The presently preferred dimensions for the capillary tube 11 are cylindrical with an inner diameter of 1.6 mm and a length of 19 mm, although other dimensions and shapes may be suitable. The length and inner diameter can be increased to collect a larger sample, or they can be decreased in order to wick more quickly and ensure that the receptacle holds the sample securely. The capillary tube 11 may have a circular cross-section as shown, or oval or various rectilinear shapes. It has been found that a non-circular cross-section such as a star or rectangle augments the capillary draw of the tube 11, but may be more difficult to mold. The entrance aperture 12 of capillary tube 11 protrudes outward for easier collection. Capillary tube 11 has an opposing end 13 that is in fluid connection with a testing region 20 (see below). The walls of the capillary tube 11 are relatively clear or translucent and may be demarcated by visible indicator lines, graduated markings or some other obvious feature to indicate to the user that enough blood has been acquired. In practice, a patient's blood will be drawn by a pin prick (as described below), the entrance aperture 12 of capillary tube 11 will be placed in contact with the blood, and the blood will be inducted by capillary action into the tube 11 until a sufficient quantity is collected. Once done, the capillary tube 11 serves as the temporary storage receptacle for the blood during transit from the patient to the analyzer 200.

Figure 7:
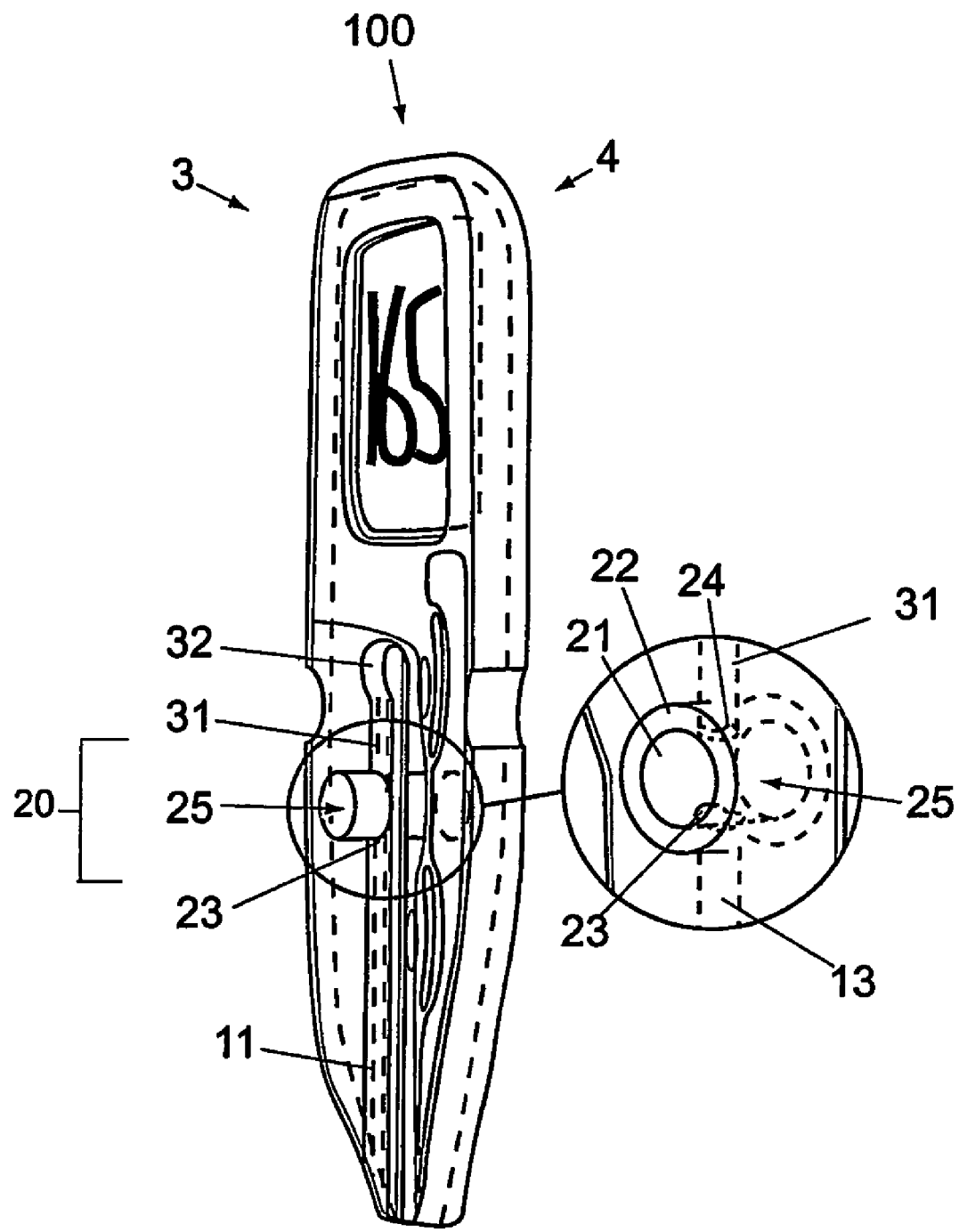
FIG. 7 is a detailed drawing of the disposable sampling device 100 of FIGS. 1-6, including an exploded view illustrating the connection between the collection region and the testing region of the disposable device 100.

FIG. 7 illustrates the connection between the opposing end 13 of tube 13 and testing region 20 of the disposable device 100. With combined reference to FIGS. 4 and 7, the testing region 20 is an open window formed by a transverse aperture 21 through the front 3 and back 4 of the supporting frame of the sampling device 100. Preferably, the aperture 21 is cylindrical to define a round-walled testing channel 25 preferably with a cylindrical cross-section. Square or rectangular cross sections are also suitable, but a cylindrical shape (round aperture with flat sides) deters air bubbles from forming in the defining a testing channel 25, while also minimizing the amount of blood required for accurate testing. The rims surrounding the aperture 21 on both the front 3 and back 4 surfaces are slightly raised to form sealing rings 22 (see FIG. 4) against the walls of the analyzer 200. This way, when the sampling device 100 is inserted into the analyzer 200 and the closure 203 is latched shut to lock the sampling device 100 in place, it is squeezed tightly between two walls of the sampling chamber inside the analyzer 200, said walls mating with the sealing rings 22 to hermetically seal off the testing channel 25. Depending on the particular analyzer for which the device is designed, the volume of the sealed testing channel 25 may range from 0.01 to 1 ml.

The passage of the capillary tube 11 traverses the testing channel 25 at two holes 23, 24 located opposite each other. The far hole 24 continues into the actuator region 30 via a hollow actuator tube 31. As shown in FIG. 4, the actuator tube 31 leads to an actuator orifice 32 that is open through the front of the sampling device 100. Orifice 32 seals over a connection to a small micro-pump in analyzer 200 that, when activated, draws the blood sample from capillary tube 11 into the sealed testing channel 25.

A substantially vertical orientation of the device 100 is maintained while in the analyzer 200 so that any entrapped air bubbles will migrate up the capillary tube 11 through the testing channel 25 and out the orifice 32.

The actuator tube 31, including ends 34 and 35, is integrally molded (or attached and sealed) at end 34 to the edges of hole 24 of testing channel 25, and this may be accomplished by molding and welding two half-sections or by unitary molding of the entire device 100. In a similar manner to the raised rims around the testing aperture 21, a raised rim exists around the actuating orifice 32. As the sampling device 100 is inserted into the analyzer 200, this rim forms a seal around a mating hole on the wall of the analyzer (not shown), allowing the actuator to communicate with the sampling device and pull the fluid up from the collecting region into the testing region.

One side 6 of the supporting structure has a pair of crescent-shaped apertures 45. Crescent-shaped apertures 45 add resiliency and allow a degree of compression against the closure 203, helping to create a positive latching effect and securely seating the device 100 in the analyzer 200.

The front 3 and back 4 surfaces of the supporting structure proximate the top end 1 include one or more raised or textured finger grips or raised text 37 (i.e. ridges or bumps) to help prevent dropping of the device during blood collection and transfer to the analyzer 200.

While the preferred embodiment of the invention is made generally of hard rubber with integral rubber sealing rings 22, one skilled in the art will understand that the device 100 may be formed substantially of hard plastic with separate rubber grommet-type sealing rings 22. Other possible materials include glass, polystyrene, polyamide, polyvinylchloride, polycarbonate, silicone, polypropylene, polyurethane, latex or polyethylene. The choice of materials and surface finishes for the device 100 are preferably chosen to prolong the onset of coagulation (i.e. Pebax). This is particularly desirable when using untreated capillary blood in an ultrasonic analyzer because it has been demonstrated that the biochemical process of coagulation changes the speed of sound over time. Surface finishes are preferably smooth to minimize the surface area, allowing the blood to flow more freely through the device and prolong the onset of coagulation.

If it is anticipated that the time between drawing blood and test completion will be significant (i.e. longer than 2 minutes, thereby causing coagulation which effects the speed of sound through the blood), powdered heparin anticoagulant, EDTA or other anticoagulants, may be coated inside the device to retard coagulation without distorting red blood cells.

The sampling device 100 may be manufactured by one-shot molding, or two-shot molding of separate halves that are then hot-welded together, the sealing rings 22 and other flexible components being integrally molded or added separately. The various parts may be connected by snaps, adhesive, ultrasonic welding, or any other method of securing differing plastic or rubber materials. The sampling device 100 may also be formed using blow molding.

Operation of the Device

Figure 8:
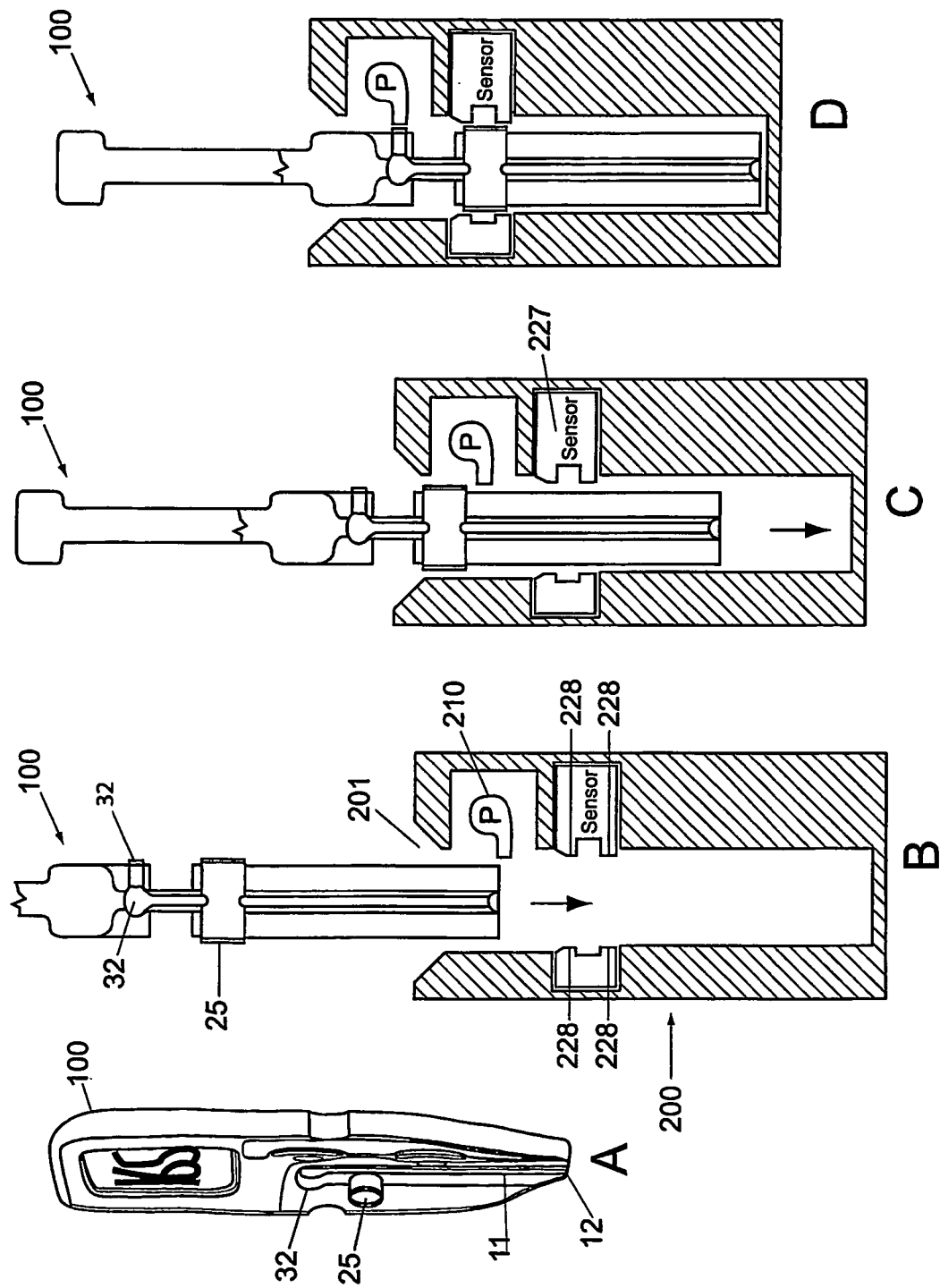
FIG. 8 is an operational sequence diagram of the disposable device 100 as used in conjunction with portable blood analyzer 200.

FIG. 8 is an operational sequence diagram of the preferred embodiment of the disposable device 100 as used in conjunction with portable blood analyzer 200.

As stated above, the preferred embodiment of the sampling device 100 is suitable for docking with any fluid analyzer equipped with an insertion port 201 as shown in FIG. 2, and capable of analyzing the small sample collected in the testing channel 25. The Ultracrit™ ultrasonic blood analyzer referenced above and shown in FIG. 1 is but one example.

In use, a blood sample is obtained by lancing the skin (i.e. by finger, heel or ear lobe stick) to obtain a capillary blood sample. As shown at (A), the end 12 of capillary tube 11 is placed immediately adjacent to the incision site and the blood is drawn into capillary tube 11 by capillary action. When the user sees through the clear or translucent capillary tube 11 that enough blood has entered the tube (e.g., blood has reached indicator line 15 or end of the tube), the device is moved away from the incision site. Capillary tube 11 serves as the temporary storage receptacle, until the device 100 can be inserted into analyzer 200 for analysis. Reducing the time between blood draw and completion of the analysis to less than 2 minutes reduces the influence of coagulation on the speed of sound traveling through blood and, thus, the results of ultrasonic blood analysis.

The frame structure of the device 100 is specifically designed to mate with port 201 of the analyzer 200 (See FIGS. 1 and 2), and the port 201 requires certain structure to work with the device 100. The port 201 structure includes the closure 203 hinged to the main body of the unit 200 and closing and latching shut to capture and seat the sampling device 100 inside with one or more Sensors 227 directed orthogonally through (and sealing off) the test channel 25 as shown in FIG. 8(B).

Thus, the device 100 is inserted into port 201 with blood sample already in the capillary tube 11. The port 201 contains one or more sensors 227 having raised sensing surfaces 228 that engage the sealing rings 22 of device 100, the sealing rings 22 acting as a wiping mechanism, cleaning the parallel sensing surfaces 228 of the sensors 227 within the analyzer 200. When fully inserted, the device 100 bottoms out on the closure 203 guaranteeing that the device 100 is located correctly with respect to the sensing surfaces 228. The sealing rings 22 then form a hermetic seal against the sensing surfaces 228, thereby forming a closed testing chamber 25. FIG. 8(D) illustrates the final position of the device 100 with micropump 210 facing the actuator region 30 and raised sensing surfaces 228 around Sensor 227 engaged with the sealing rings 22 so that the sensor 227 communicates with the testing channel 25. The crescent apertures 45 also help in seating device 100 as positive latching occurs just after they have been compressed a bit.

Again, latching the closure 203 activates a microswitch (not shown) that in turn initiates a pumping sequence at micro-pump 210 to draw the blood in capillary tube 11 into the test channel 25. As seen at FIG. 8(D), the micro-pump 210 engages actuator orifice 32 and sucks the blood sample out of capillary tube 11 into testing chamber 25.

Figure 9:
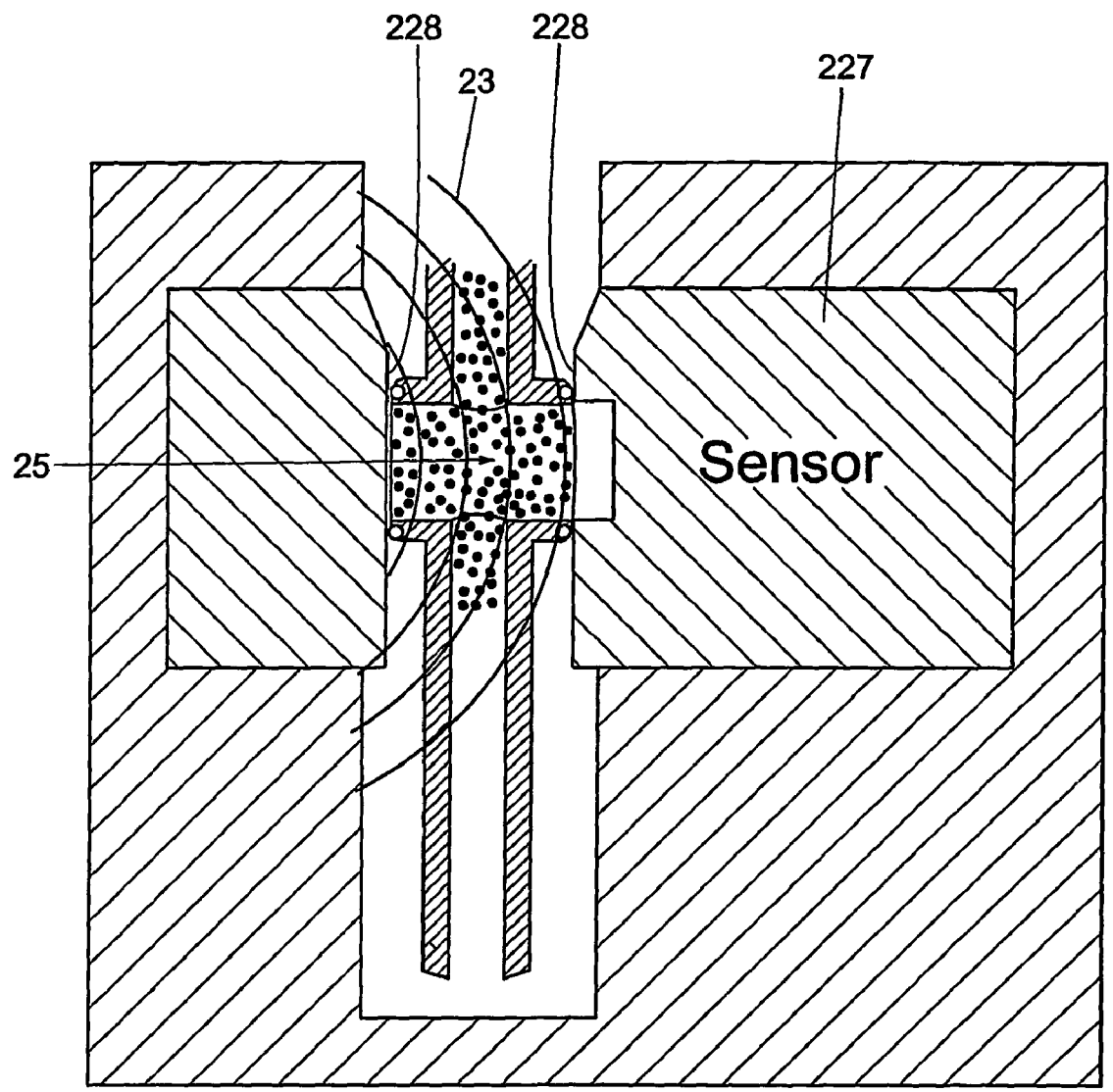
FIG. 9 is an operational schematic drawing illustrating the interface between the device 100 and analyzer 200.

FIG. 9 is an operational schematic drawing illustrating the interface between the device 100 and analyzer 200, and operation of the portable blood analyzer 200 after insertion of the present disposable collection and testing device. In the illustrated embodiment the open but sealed testing chamber 25 allows the blood to directly contact the parallel sensing surfaces of the sensor 227 to optimize the measurement by improving accuracy of the measurement, and of temperature control. The illustrated sensor 228 is an ultrasonic sensor which emits ultrasonic frequencies through the testing chamber 25 and measures the reflections. It is also envisioned that a temperature measurement will be made. Once the analysis is complete, the micro-pump 210 exerts a small amount of reverse pressure to force the blood out of the testing chamber 25 and back into capillary tube 11. As the device 100 is removed from the analyzer 200, the sealing rings 22 again serve as a wiping mechanism, cleaning off the sensing surfaces 228. The danger of inadvertent exposure to the blood is eliminated by the sequential use of capillary action and pressure-differential to move the blood from containment, to sample chamber, and back, automatically upon insertion and withdrawal.

Additional Embodiments

Figure 10:
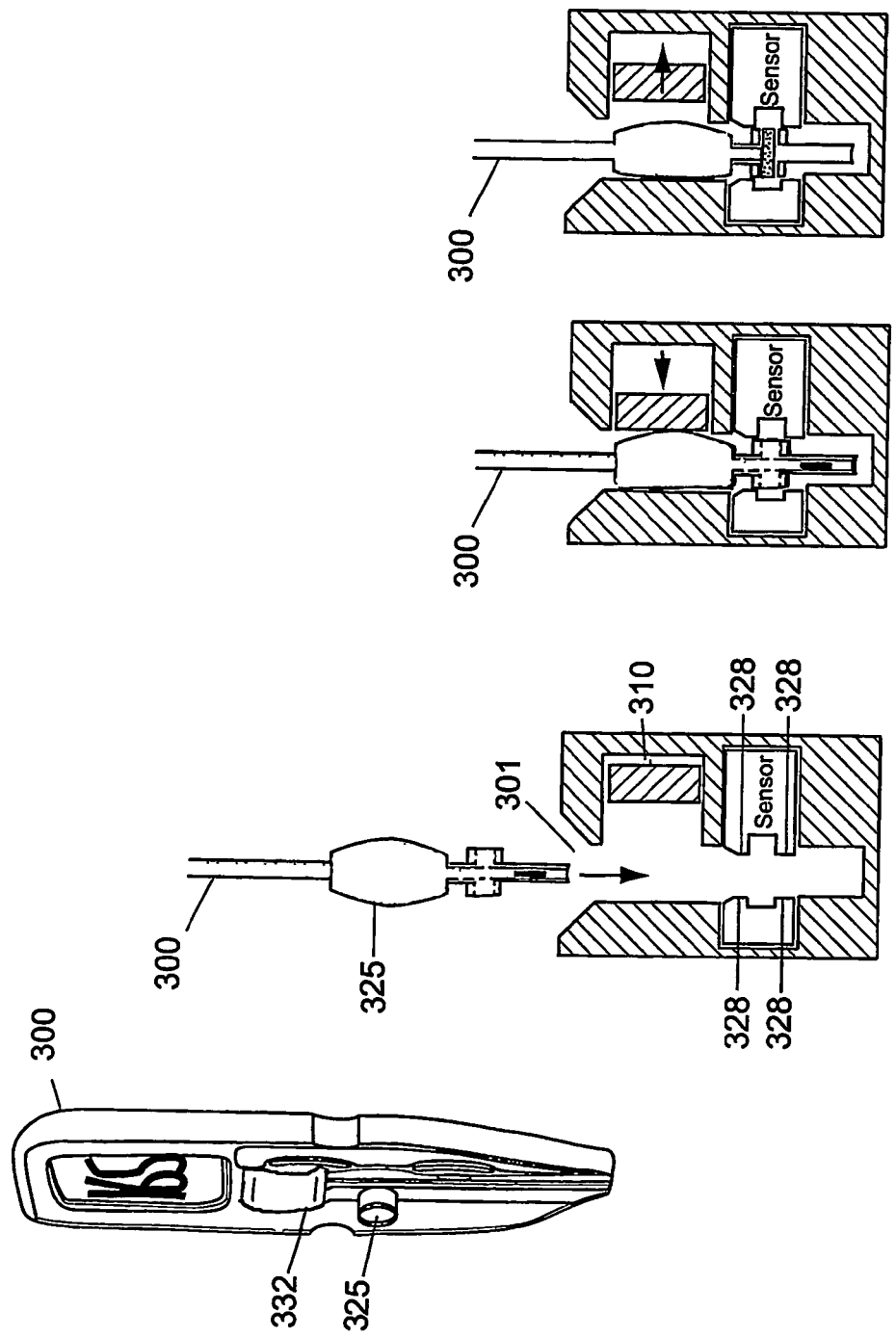
FIG. 10 is a perspective operational sequence diagram of an alternative embodiment of the disposable device 300 in which the pump is replaced by an actuator bulb 332.

While the embodiment of FIGS. 1-8 relies on a pump 210, FIG. 10 shows an alternative embodiment 300 in which the external pump is replaced by an on-board actuator bulb 332. The actuator bulb 332 is preferably made of flexible rubber or plastic and may be integrally molded in the front 3 and back 4 surfaces of the sampling device 300 (by molding and welding two half-sections or by unitary molding of the device 300). The actuator bulb 332 is sealed and feeds a pressure differential through a connected actuator tube 331 into testing chamber 325. The actuator bulb 332 protrudes above the plane of the device 300 such that when the device 300 is inserted into port 201 with blood sample already in the capillary tube 11, the analyzer 200 squeezes and releases the bulb 332. As before, sealing rings 322 around the test chamber 325 act as a wiping mechanism against the sensor housing surfaces 328 (which contain one or more sensors 327) within the analyzer 300. Analyzer 200 may comprise a mechanism 310 for that depressing and releasing the actuator bulb 32 as shown (this may be a conventional solenoid). Alternatively, the port 201 may be formed with constricted sides (or protrusions) at a predetermined depth. Thus, as device 300 is inserted, the sides of the port 301 depress the actuator bulb 332 forcing air through actuator tube 331 into testing cylinder 325 and out apertures 321, and then release the bulb 332 as the bulb travels past. This creates a vacuum which draws the blood stored in the capillary tube 311 into the testing chamber 326. Once the analysis is complete, the sampling device 300 is withdrawn, the sides of the port 321 are again positioned to depress the actuator bulb 331, thus using air pressure to force the blood out of the testing chamber 326 and back into capillary tube 311. As the device 300 is removed from the analyzer 200, the sealing rings 322 again serve as a wiping mechanism, cleaning off the sensing surfaces 328. The danger of inadvertent exposure to the blood is eliminated by the sequential use of capillary action and pressure-differential to move the blood from containment, to sample chamber, and back, automatically upon insertion and withdrawal.

In the preferred embodiment, the raised seals 22 around the testing chamber 25 are distinct from the raised seals around the actuator region. In an additional embodiment, these seals could be combined to form one large oval shaped seal which circumscribes both the Sensors 227 and the micropump 210, thus shortening the distance between the testing region and actuator region. This would help to lower the required force of pushing the analyzer into the device.

In all the above-described embodiments the collection region 10, testing region 20 and the actuation region 30, respectively, have been oriented vertically from the bottom 2 to the top 1 of the supporting frame 7 of the device. However, this orientation is not a functional requirement. The orientation of the functional regions of the device (i.e. the collection region 10, the testing region 20 and the actuation region 30) may be changed depending on the structure of particular analyzer with which the device will interface.

Figure 11:
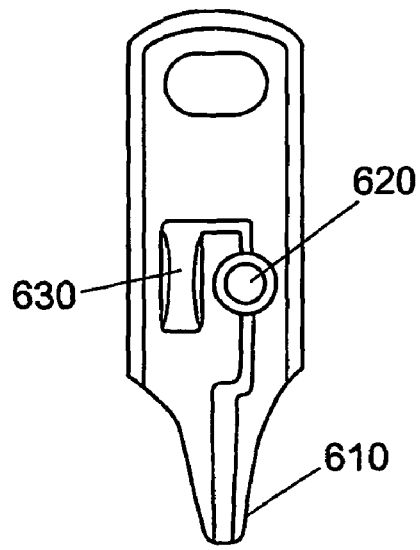
FIG. 11 is a front view of another alternative embodiment in which the testing region 620 and the actuation region 630 are side-by-side above the collection region 610.

FIG. 11 illustrates an embodiment in which the testing region 620 and the actuation region 630 are side-by-side above the collection region 610.

Figure 12:
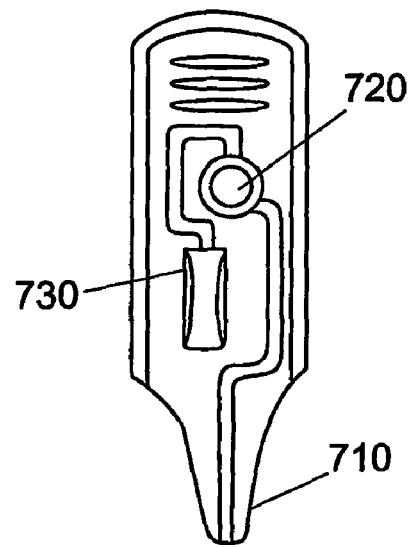
FIG. 12 is a front view of another alternative embodiment in which the functional regions are oriented vertically with the collection region 710 at the bottom, the actuation region 730 in the middle and the testing region 720 at the top.

FIG. 12 illustrates an embodiment in which the functional regions are oriented vertically with the collection region 710 at the bottom, the actuation region 730 in the middle and the testing region 720 at the top.

Figure 13:
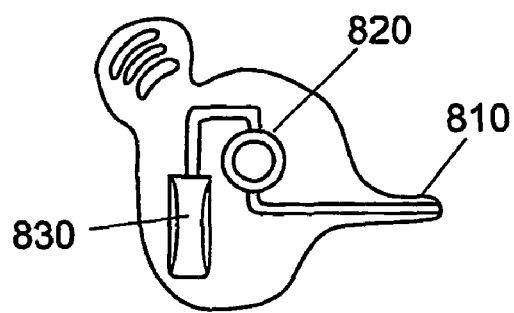
FIG. 13 is a front view of another alternative embodiment in which the device is designed to be inserted horizontally into a side port on an analyzer 200.

FIG. 13 illustrates an embodiment in which the device is designed to be inserted horizontally into a side port on an analyzer. In this embodiment the functional regions are also oriented horizontally.

Figure 14:
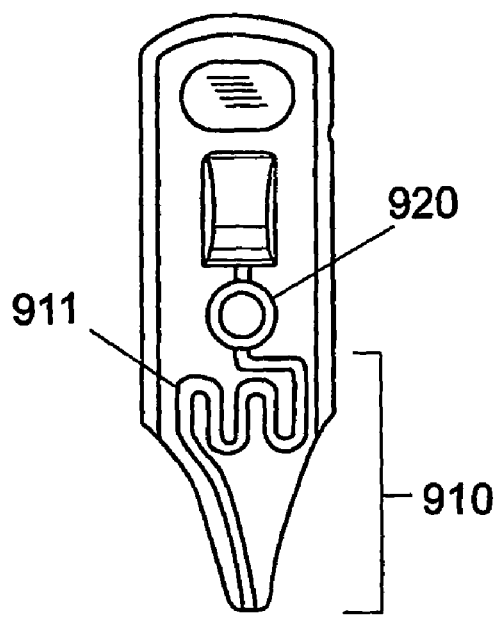
FIG. 14 is a front view of another alternative embodiment in which the capillary tube 911 is curvilinear and extended.

FIG. 14 illustrates an alternative embodiment in which the collecting region 910 includes a capillary tube 911 that is significantly extended relative to the capillary tube 11 of FIGS. 3-6, as much as 100 mm long. To accommodate the additional length, the capillary tube 911 is formed in a curvilinear path, in this case curving up and down several times before connecting to testing region 920.

Figure 15:
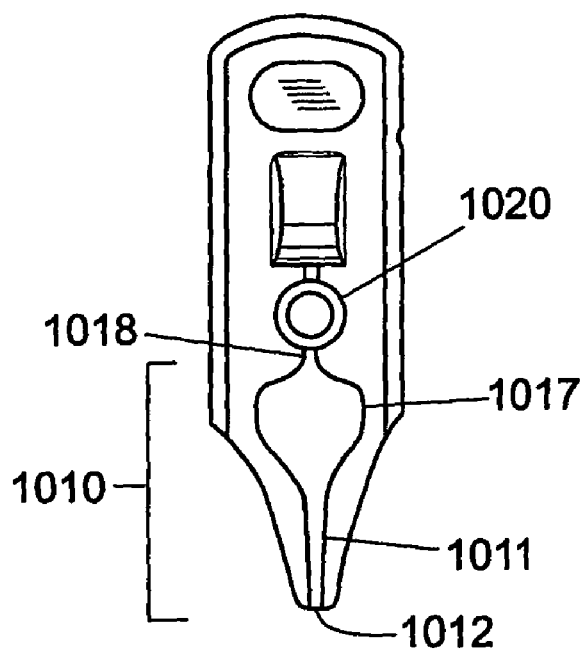
FIG. 15 is a composite view of another alternative embodiment in which the capillary tube expands forming a wide flat cavity 1017 leading to another capillary tube 1018 which connects to the testing region.

FIG. 15 illustrates an embodiment in which the collecting region 1010 includes a small aperture 1012 defining the entrance of a capillary tube 1011. The capillary tube then expands forming a wide flat cavity 1017 leading to another capillary tube 1018 which connects to the testing region. The wide top and bottom parallel plates of this flat cavity 1017 provide a large surface area that promotes thermal equilibrium while also deterring the formation of bubbles. Yet another embodiment (not shown) of the invention that is designed to hasten temperature equilibrium includes a piece of metal incorporated into the support frame of the device which would come in direct or close contact with the blood in order to more quickly equilibrate the blood temperature to ambient temperature.

Figure 16:
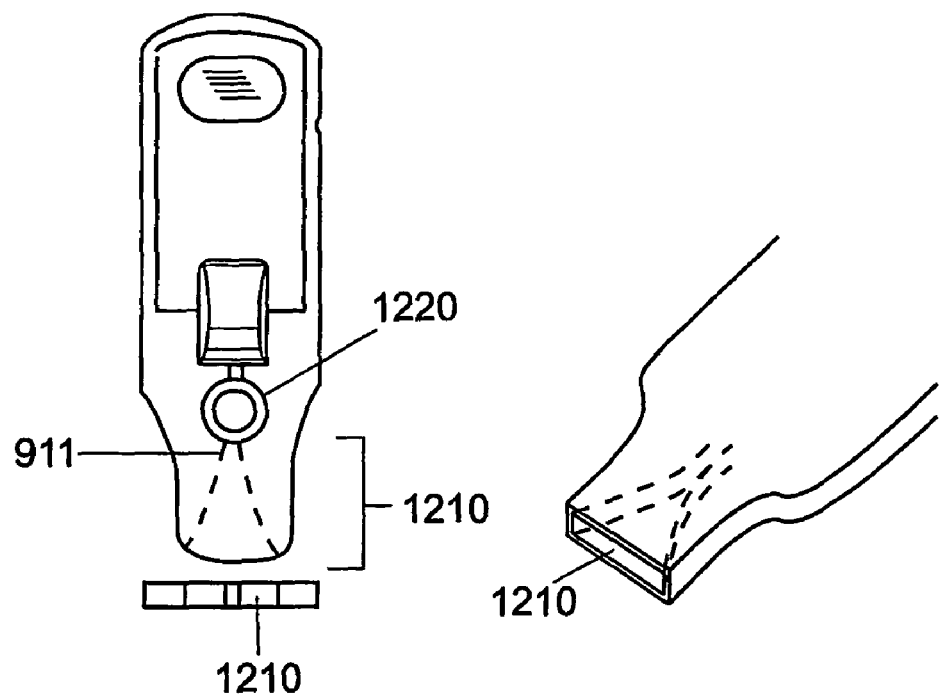
FIG. 16 is a composite view of another embodiment having a wide but narrow rectangular aperture 1212 defining the entrance through which blood flows into the device.

FIG. 16 illustrates an embodiment with a rectangular aperture 1212 and fluted capillary tube 911 defining the entrance through which blood flows into the device. If the rectangular aperture is narrow enough (roughly 1 mm or less on its shorter dimension), it will hold the sample securely by capillary action, just like the cylindrical capillary tube holds the sample. The blood is then immediately funneled into a narrow tube 1211 which connects to the testing region 1220.

Figure 17:
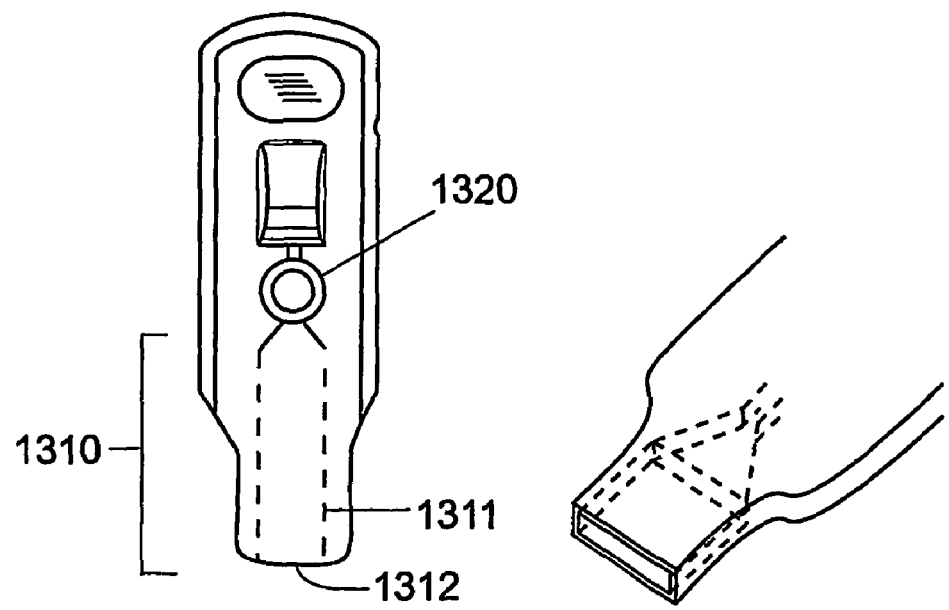
FIG. 17 is a composite view of another embodiment in which the entrance aperture 1312 joins a rectangular channel 1311 which funnels at the opposite end into the testing region 1320.

FIG. 17 illustrates another embodiment in which the entrance aperture 1312 is rectangular and the capillary tube 1311 straight and thin, to a funnel into the testing region 1320.

In light of the foregoing it should be clear that the configuration, length and shape of the collection region may be varied to serve varied purposes, e.g., to increase the surface area over which the blood passes in order to hasten thermal equilibrium between the blood and the device, to minimize air bubbles, simply to collect a larger sample, or to decrease the sample in order to wick quickly and ensure that the receptacle holds the sample securely. Another method of hastening temperature equilibrium includes cycling the blood, by depressing and releasing an actuator bulb (or by intermittent pump induction), to flow from the collection region to the testing region and back several times before commencing the analysis. This practice mixes the blood, ensuring temperature equilibrium and suspension of the RBC's during testing.

It has also been found that a tear-drop shaped testing chamber 25 (having a rounded bottom and pointed top) encourages any air bubbles to move up into the pointed top area and away from the round bottom area through which the ultrasonic measurement beam emitted by the analyzer travels.

In all of the foregoing embodiments, before the device is removed from the analyzer 200, all blood should be moved out of the testing chamber into a closed chamber to allow removal of the device without spillage. With an actuator bulb 332 this is accomplished by depressing the actuator bulb 332 during or prior to removal to force the blood out of the testing chamber 25 and back into the entrance region 10, where it remains. The same effect may be accomplished with pump 210 to force the blood out of the testing chamber 25 and back into the entrance region 10.

In all embodiments after the device is removed from the analyzer it is thrown away.

INDUSTRIAL APPLICABILITY

Blood testing is typically done with syringes and laboratory blood analyzers. However, more recent advances are resulting in portable and more convenient (less intrusive) products. There are few portable blood analyzers appearing on the market that generally accept a test strip (coated with a blood sample and reagent) or the like. However, these are extremely messy and do not safeguard the transfer of the blood sample from patient to analyzer in the least respect. There is a significant commercial demand for an all-in-one disposable device that collects and temporarily safely stores a blood sample for analysis by capillary action, and which is insertable into the testing region of a portable analyzer, the analyzer interfacing with the disposable device to initiate a pressure differential that moves the blood sample into and out of a testing chamber (still on the disposable device) whereby the blood sample is in direct contact with sensor in the analyzer. This self-contained format of the disposable device used in conjunction with the particular analyzer would provide a quick, clean and safe way of collecting and testing a predefined amount of blood (or other fluid), especially in emergency or non-laboratory settings.

Having now fully described this invention, it will be apparent to one of ordinary skill in the art that many changes and modifications can be made thereto without departing from the spirit or scope of the invention as set forth herein.

We claim:

1. A fluid sample collection device for collecting 0.05 mL or less of blood, and for insertion and testing of said blood in an ultrasonic analyzer, comprising:
   a thin elongate body having a finger-grip at one end, and another functional insertion end, said insertion end including,
      a collecting region including an entrance aperture through which fluid enters a capillary tube within said collecting region by capillary action;
      a testing region in fluid communication with said collecting region for containing at least a portion of said fluid during testing inside said ultrasonic analyzer, said testing region further comprising an open-ended cylindrical channel perpendicular to said capillary tube and passing through said thin elongate body from one external surface to another external surface, thereby defining a circular aperture into said thin elongate body adapted for sealed engagement by an external sensor in said ultrasonic analyzer, said open-ended cylindrical channel containing said portion of said fluid such that said fluid portion comes in direct contact with said external sensor while still sealed inside the testing region, and
      a pumping region in fluid communication with said testing region for introducing a pressure-differential and thereby inducting said portion of said fluid from said collecting region into said open-ended channel of said testing region wherein said portion is placed in direct contact at each open end of said channel with a sensing surface of said ultrasonic analyzer.

2. The fluid sample collection device according to claim 1, wherein said pumping region comprises a bulb for introducing said pressure-differential.

3. The fluid sample collection device according to claim 1, wherein said pumping region comprises an orifice for coupling a pump in said ultrasonic analyzer to said testing region for introducing said pressure-differential.

4. The fluid sample collection device according to claim 2, wherein said bulb is operated by insertion of said collection device into said ultrasonic analyzer and squeezing thereof during insertion.

5. The fluid sample collection device according to claim 2, wherein said bulb is operated by squeezing via an actuator in said ultrasonic analyzer.

6. A disposable blood sample collection device for insertion and testing of a blood sample in a portable ultrasonic analyzer, comprising:
   an elongate body including,
      a collecting region including an entrance aperture through which said blood sample is drawn by capillary action into a capillary tube within said collecting region,
      a testing region in fluid communication with said collecting region for containing at least a portion of said blood sample, said testing region further comprising an open-ended cylindrical channel perpendicular to said capillary tube passing through said elongate body from one external surface to another external surface, thereby defining a circular aperture in said thin elongate body adapted to be sealed off between external sensor walls of said portable ultrasonic analyzer when inserted therein such that said portion of said blood sample within said open-ended cylindrical channel is sealed within said open-ended channel and directly exposed to the external sensor walls of said ultrasonic analyzer, and
      an orifice in fluid communication with said testing region for coupling a pump inside said ultrasonic analyzer to induct said portion of said blood sample from said collecting region into the open ended channel of said testing region.

7. A disposable blood sample collection device for insertion and testing of a blood sample in a portable ultrasonic analyzer, comprising:
   an elongate body including,
      a collecting region including an entrance aperture through which a sample of blood is drawn by capillary action into a capillary tube within said collection region,
      a testing region in fluid communication with said collecting region for exposing at least a portion of said blood sample to a sensor during testing inside said ultrasonic analyzer, said testing region further comprising an open-ended cylindrical channel perpendicular to said capillary tube and passing through said thin elongate body from one external surface thereof to another, thereby defining a circular aperture in said thin elongate body adapted to be sealed off by an external sensor of said portable ultrasonic analyzer when inserted therein such that the portion of said blood sample is sealed within the cylindrical channel and is directly exposed to said external sensor, and
      a bulb in fluid communication with said testing region and manipulated by said analyzer to induct said portion of said blood sample from said collecting region into said open-ended channel of said testing region for testing wherein said blood is placed in direct contact at each open end of the channel with a sensing surface of said ultrasonic analyzer instrument.

8. The disposable blood sample collection device according to claim 7, wherein said bulb is manipulated by said ultrasonic analyzer as a result of insertion therein.

9. The disposable blood sample collection device according to claim 7, wherein said bulb is manipulated by an actuator inside said ultrasonic analyzer.

10. The disposable blood sample collection device according to claim 9, wherein said actuator comprises a solenoid.

11. A disposable blood sample collection device for insertion into an ultrasonic analyzer, comprising:
   a thin elongate body adapted for insertion into said ultrasonic analyzer;
   a capillary tube integrally-molded in said body and extending inwardly from a distal end;
   an open-sided testing region in fluid communication with said capillary tube, said testing region comprising an open-ended cylindrical channel passing through said thin elongate body perpendicular to said capillary tube from one external surface of said body to another, thereby defining a circular aperture in said thin elongate body adapted to be sealed off by an external sensor of said portable ultrasonic analyzer when inserted therein such that at least a portion of a blood sample is sealed within the cylindrical channel and therein directly exposed to said external sensor; and
   an actuator region in fluid communication with said testing region for introducing a pressure-differential and thereby inducting said portion of said blood sample from said capillary tube into said open-ended channel of said testing region wherein said portion is placed in direct contact with said sensing walls within said ultrasonic analyzer.

12. The disposable blood sample collection device according to claim 11, wherein said capillary tube is pre-loaded with anticoagulant.

13. The disposable blood sample collection device according to claim 11, wherein said thin elongate body comprises at least one edge which communicates with said ultrasonic analyzer to correctly position said disposable blood sample collection device with respect to said analyzer.

* * * * *